United States Patent
Schmidt

(10) Patent No.: US 9,888,877 B2
(45) Date of Patent: Feb. 13, 2018

(54) METHOD AND COMPUTER AND IMAGING APPARATUS FOR EVALUATING MEDICAL IMAGE DATA

(71) Applicant: Siemens Aktiengesellschaft, Munich (DE)

(72) Inventor: Sebastian Schmidt, Weisendorf (DE)

(73) Assignee: Siemens Aktiengesellschaft, Munich (DE)

(*) Notice: Subject to any disclaimer, the term of this patent is extended or adjusted under 35 U.S.C. 154(b) by 88 days.

(21) Appl. No.: 15/001,461

(22) Filed: Jan. 20, 2016

(65) Prior Publication Data

US 2016/0210743 A1 Jul. 21, 2016

(30) Foreign Application Priority Data

Jan. 20, 2015 (DE) .................. 10 2015 200 850

(51) Int. Cl.
*G06K 9/00* (2006.01)
*A61B 5/00* (2006.01)
*G06T 7/00* (2017.01)
*G06T 7/68* (2017.01)

(52) U.S. Cl.
CPC .......... *A61B 5/4064* (2013.01); *G06T 7/0014* (2013.01); *G06T 7/68* (2017.01); *G06T 2207/10088* (2013.01); *G06T 2207/20224* (2013.01); *G06T 2207/30016* (2013.01); *G06T 2207/30096* (2013.01)

(58) Field of Classification Search
CPC ...... A61B 3/1241; A61B 6/504; G01R 33/56; G01R 33/5635; G06T 2211/404
See application file for complete search history.

(56) References Cited

U.S. PATENT DOCUMENTS

| | | | | |
|---|---|---|---|---|
| 6,067,373 A * | 5/2000 | Ishida | ................... | G06T 3/0068 378/98.12 |
| 6,075,879 A * | 6/2000 | Roehrig | ................ | G06F 19/321 128/922 |
| 6,594,378 B1 * | 7/2003 | Li | ......................... | G06T 3/0068 128/922 |
| 7,653,263 B2 * | 1/2010 | Wheeler | ................. | G06T 7/001 382/294 |
| 7,724,931 B2 * | 5/2010 | Kuth | .................... | G06K 9/6206 382/128 |
| 8,331,637 B2 * | 12/2012 | Bar-Aviv | .............. | G06F 19/321 382/128 |
| 9,082,231 B2 * | 7/2015 | Zhou | ....................... | G06T 11/60 |
| 9,401,021 B1 * | 7/2016 | Biagiotti | ............... | G06T 7/0014 |

(Continued)

Primary Examiner — Avinash Yentrapati
(74) Attorney, Agent, or Firm — Schiff Hardin LLP

(57) ABSTRACT

In a method, an evaluation computer, and a medical imaging apparatus for evaluating medical images of an organ system of an examination subject, wherein the organ system has a first side and a second side that are characteristically bilaterally symmetrical to one another, first and second medical image datasets of the organ system of the examination subject are acquired and processed to obtain a result image dataset by a global image data subtraction in which image components of the first and second medical image data are subtracted from one another, and a symmetry subtraction in which image components of the first side and the second side of the organ system are subtracted from one another within a medical image dataset.

9 Claims, 3 Drawing Sheets

(56) References Cited

U.S. PATENT DOCUMENTS

| | | | |
|---|---|---|---|
| 2001/0053240 A1* | 12/2001 | Oosawa | G06K 9/6203 |
| | | | 382/128 |
| 2002/0196965 A1* | 12/2002 | Wallace | A61B 5/0059 |
| | | | 382/128 |
| 2005/0283070 A1* | 12/2005 | Imielinska | A61B 6/032 |
| | | | 600/425 |
| 2007/0003117 A1* | 1/2007 | Wheeler | G06T 7/001 |
| | | | 382/128 |
| 2007/0161886 A1* | 7/2007 | Kuth | G06K 9/6206 |
| | | | 600/407 |
| 2008/0021502 A1* | 1/2008 | Imielinska | A61B 6/032 |
| | | | 607/1 |
| 2008/0292194 A1* | 11/2008 | Schmidt | G06T 7/0012 |
| | | | 382/217 |
| 2010/0098305 A1* | 4/2010 | Burns | G06T 7/33 |
| | | | 382/128 |
| 2010/0259263 A1* | 10/2010 | Holland | A61B 5/055 |
| | | | 324/310 |
| 2014/0044336 A1 | 2/2014 | Heinlein et al. | |
| 2015/0178938 A1* | 6/2015 | Gorman, III | G06T 7/0087 |
| | | | 382/131 |

* cited by examiner

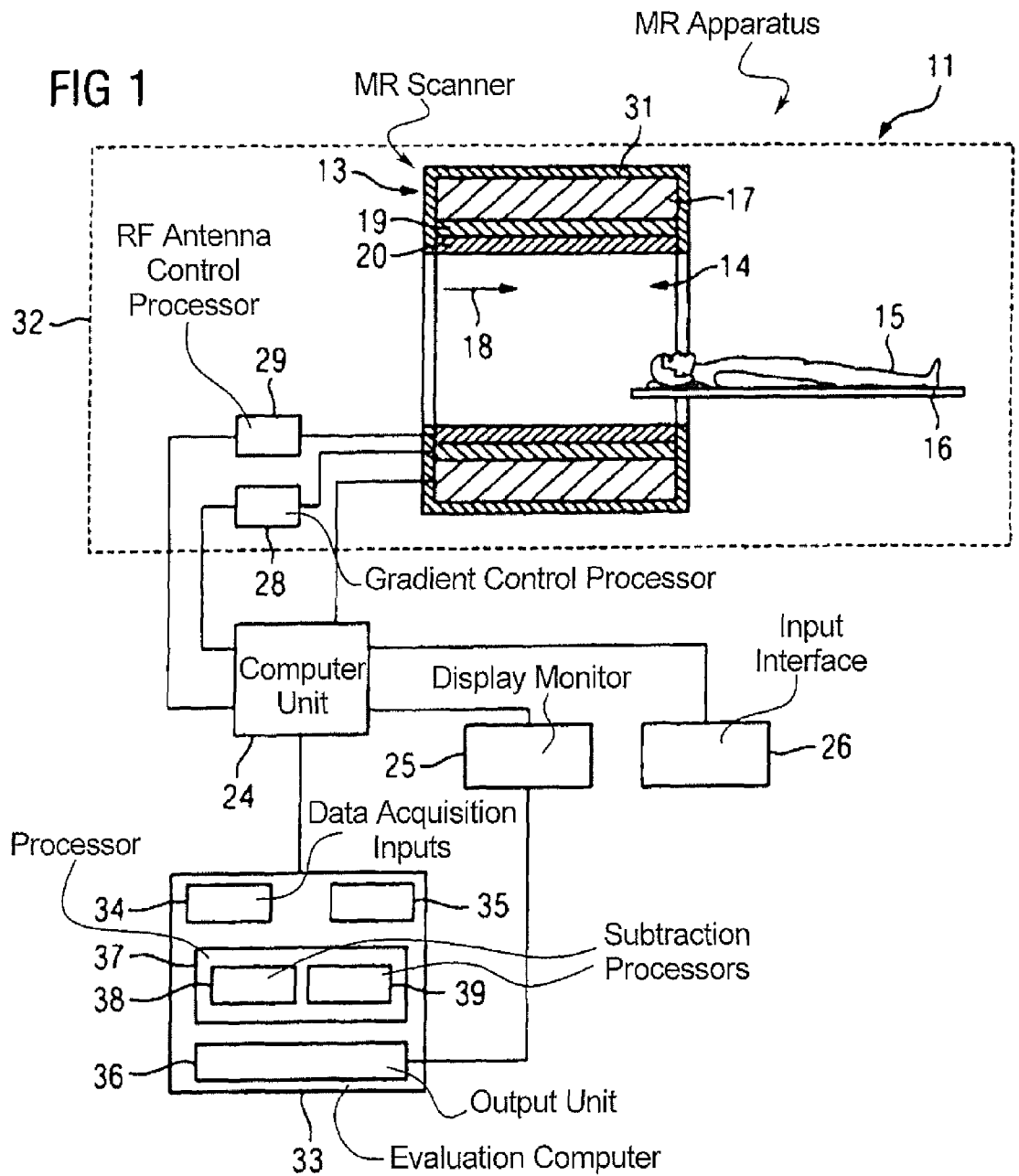

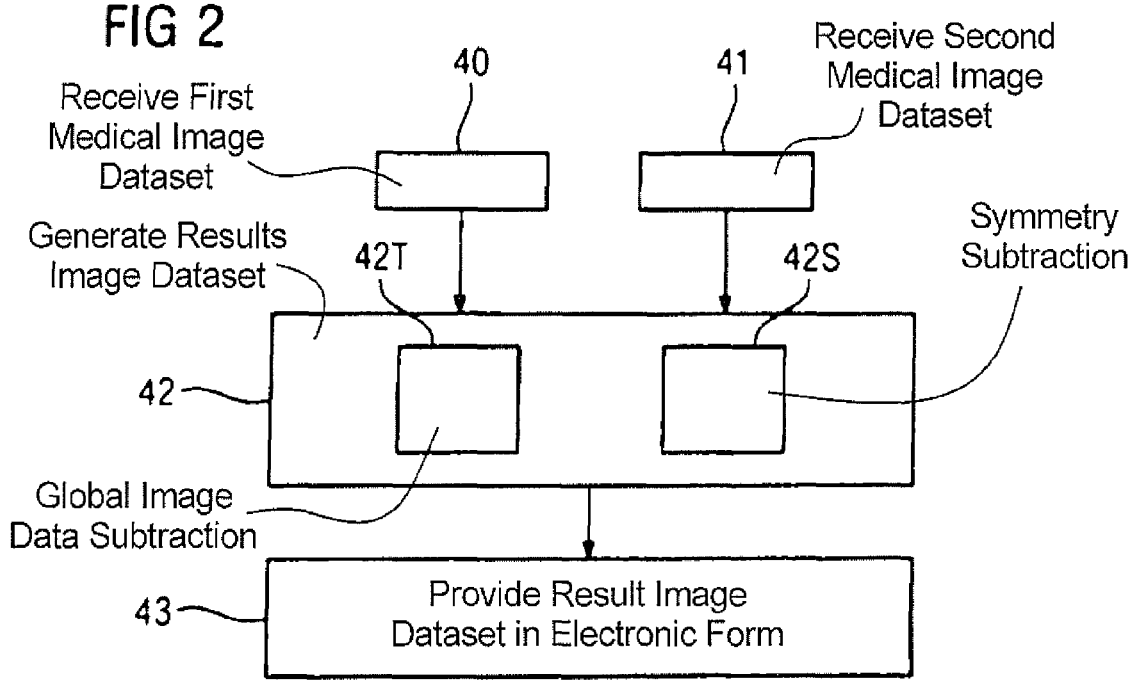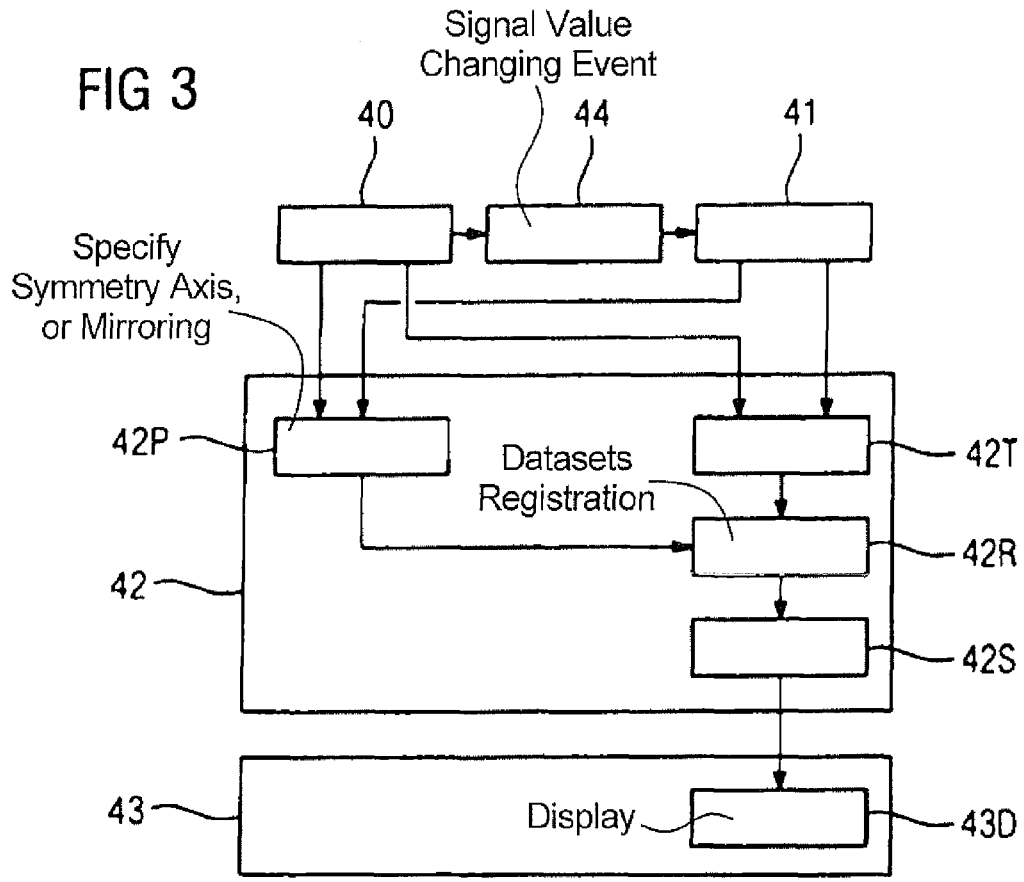

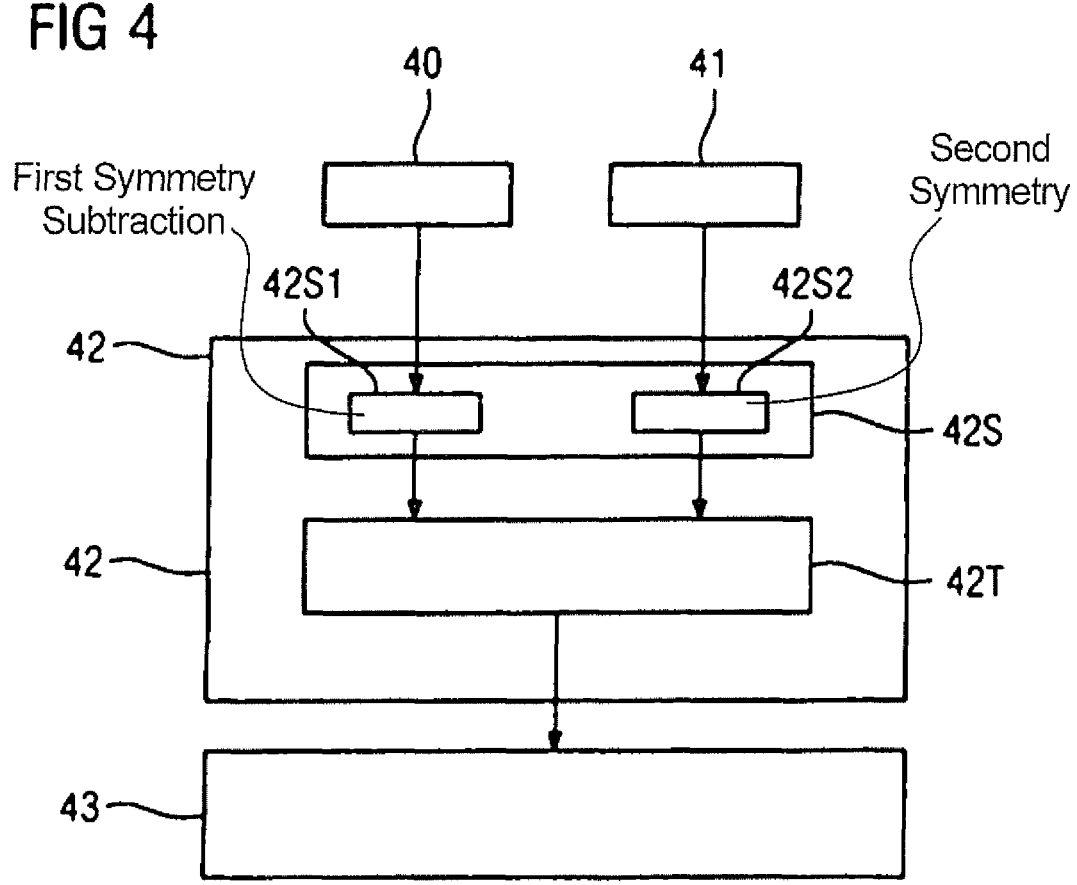

METHOD AND COMPUTER AND IMAGING APPARATUS FOR EVALUATING MEDICAL IMAGE DATA

BACKGROUND OF THE INVENTION

Field of the Invention

The invention concerns a method for evaluating medical image data, and an evaluation computer, a medical imaging apparatus, and a non-transitory, computer-readable data storage medium for implementing such a method.

Description of the Prior Art

Medical image data are normally acquired by medical imaging apparatuses and can represent anatomical structures and/or functional processes of the body of an examination subject. Medical image data of a single examination subject often are composed of medical image datasets that have been recorded at different points in time, for example. A typical problem to be addressed in this regard is how to compare the multiple medical image datasets with one another and identify variations between the multiple medical image datasets. For example, a characteristic of a change in the body of the examination subject as a function of time can be determined in a dynamic measurement.

In a perfusion imaging procedure, for example, there are typically a number of chronologically sequential medical image datasets available that describe a change in the content of a contrast agent in a tissue of the examination subject. A metric for a blood flow through the tissue can be derived therefrom.

In functional magnetic resonance imaging, signal variations between a number of medical image datasets typically indicate changes in the local oxygen uptake rate. From this it is possible to derive a metric for a change in the activity of functional centers in the brain of the examination subject, particularly in relation to a reaction to specific stimuli, such as optical stimuli.

Dynamic nuclear medical measurements, such as dynamic positron emission tomography (PET) measurements, are also known. In this case it is possible to measure the distribution of certain tracers, such as fluorodeoxyglucose, in the body of the examination subject over time.

Other medical imaging methods in which a number of medical image datasets of an examination subject are acquired, and are to be compared, are known to those skilled in the art.

Typically, it is difficult to detect minor variations between the number of medical image datasets in a qualitative sense. Dynamic measurements in particular are often limited in their signal-to-noise ratio due to their temporal resolution, with the result that variations in the medical image datasets are frequently hidden in the image noise.

SUMMARY OF THE INVENTION

An object of the invention is to enable an improved evaluation of medical image data composed of a number of medical image datasets.

The method according to the invention for evaluating medical image data, which image an organ system of an examination subject wherein the organ system has a first side and a second side that are bilaterally symmetrical to one another with respect to anatomical characteristics, includes the following steps.

A first medical image dataset of the organ system of the examination subject is acquired and a second medical image dataset of the organ system of the examination subject is also acquired. The first medical image dataset and the second medical image dataset are processed to obtain a result image dataset that is provided as a data file for viewing. The processing of the first medical image dataset and the second medical image dataset includes a global image data subtraction in which image components of the first medical image data and the second medical image data are subtracted from one another, and a symmetry subtraction in which image components of the first side and second side of the organ system are subtracted from one another within a medical image dataset.

The examination subject may be a patient, a training volunteer or a phantom. The organ system is characteristically bilaterally symmetrical with respect to a plane of symmetry. Thus, the first side of the organ system lies on a first side of the plane of symmetry and the second side of the organ system lies on a second side of the plane of symmetry. Typically, the organ system is characteristically bilaterally symmetrical with respect to a sagittal plane of symmetry. In a human examination subject, such a sagittal plane of symmetry typically extends from the head to the pelvis of the examination subject and from the spine to the abdomen of the examination subject. Typically, the plane of symmetry runs through the center of the examination subject's body and can therefore be referred to as the median plane.

The method according to the invention can be applied in an imaging of the brain of the examination subject, as a bilaterally symmetrical organ. The first side of the organ system can then be the left cerebral hemisphere and the second side of the organ system can be the right cerebral hemisphere. The reverse case is, of course, also possible. Other possible bilaterally symmetrical organs are, for example, a part of the skeletal system and/or muscular system of the examination subject, a pair of eyes of the examination subject, a pair of breasts of the examination subject, a pair of kidneys of the examination subject, a pair of lungs of the examination subject, etc. Other bilaterally symmetrical organs are also known to those skilled in the art. It should be noted that a perfect bilateral symmetry is practically unheard of in nature. Typically, therefore, the first side and the second side of the organ system are characteristically substantially bilaterally symmetrical to one another, meaning that deviations from perfect bilateral symmetry are diagnostically irrelevant. For example, the first side and the second side of the organ system may be considered perfectly bilaterally symmetrical and/or mirror-symmetrical only after being brought into registration to one another, such as by a non-rigid registration.

The acquisition of the first medical image dataset and/or the second medical image dataset can take place by operation of a medical imaging apparatus, particularly a scanner thereof. Alternatively, the acquisition of the first medical image dataset and/or the second medical image dataset can be the loading of an already-recorded first medical image dataset and/or an already recorded second medical image dataset from an image database.

The first medical image dataset and the second medical image dataset map represent the same organ system of the same examination subject. The first medical image dataset and the second medical image dataset may have been recorded at different points in time by a medical imaging device. A relatively long period of time may elapse between the recording of the first medical image dataset and the recording of the second medical image dataset. Thus, the first medical image dataset and the second medical image dataset may have been recorded in different measurements, on different days, for example. Alternatively, the first medical image dataset and the second medical image dataset may have been recorded in a single, dynamic, measurement. A relevant event may occur between the recording of the first medical image dataset and the second medical image dataset. Such a relevant event may be, for example, a stimulus, such as an optical or acoustic stimulus, to the examination subject, an administration of contrast agent or some other intervention. In this case the first medical image dataset may have been recorded at a point in time prior to the second medical image dataset or vice versa.

The processing of the first medical image dataset and the second medical image dataset is implemented by an algorithm in a computer. In this case the algorithm receives the first medical image dataset and the second medical image dataset as input parameters. The algorithm generates the result image dataset as an output. The provision of the result image dataset can be displaying the result image dataset for a user on a display monitor and/or storing the result image dataset in a database. The result image dataset includes information that represents a change in the contents of an image between the first medical image dataset and the second medical image dataset.

In accordance with the invention, the processing of the first medical image dataset and the second medical image dataset includes two subtractions, i.e. the global image data subtraction and the symmetry subtraction. The processing may also involve further processing steps, for example further subtractions. Preferably, the global image data subtraction is performed first, followed by the symmetry subtraction. It is also possible, however, for the symmetry subtraction to be performed first, and then the global image data subtraction.

Image components of both the first medical image dataset and the second medical image dataset are used for the global image data subtraction. The global image data subtraction therefore constitutes a subtraction with respect to time. By the global image data subtraction, it is therefore possible to identify changes over time between the recording of the first medical image dataset and the recording of the second medical image dataset. In this case, image components of the first medical image dataset can be subtracted from image components of the second medical image dataset, or vice versa. If the global image data subtraction is performed before the symmetry subtraction, then the first medical image dataset and the second medical image dataset are incorporated unchanged into the global image data subtraction. If the global image data subtraction is performed after the symmetry subtraction, image components of the first medical image dataset and the second medical image dataset that changed in the symmetry subtraction are incorporated as input parameters in the global image data subtraction.

It may be beneficial in this regard to align the image components of the first medical image dataset and the second medical image dataset to one another, for example by a registration, for the purpose of the global image data subtraction. This enables movements of the examination subject that have occurred between the recording of the first medical image dataset and the second medical image dataset to be at least partially compensated for. It is also possible for more than two medical image datasets of the examination subject to be acquired. In that case, a number of global image data subtractions can be performed. It is also possible for a number of medical image datasets to be merged into an averaged medical image dataset for the subsequent post-processing operation. Other processing steps deemed beneficial by those skilled in the art can also be performed during the global image data subtraction.

The symmetry subtraction takes place within a single medical image dataset. If the symmetry subtraction is performed before the global image data subtraction, two symmetry subtractions will advantageously be performed separately in each case in the first medical image dataset and in the second medical image dataset. If the symmetry subtraction is performed after the global image data subtraction, the symmetry subtraction will advantageously be performed within a result image dataset of the global image data subtraction, referred to as a global image data subtraction image dataset.

In the symmetry subtraction, the first side of the organ system is subtracted from the second side of the organ system, or vice versa. Thus, halves of the organ system that are bilaterally symmetrical to one another are subtracted from one another in the symmetry subtraction. In the case of brain imaging, for example, one cerebral hemisphere of the examination subject is subtracted from the other cerebral hemisphere in the symmetry subtraction. The symmetry subtraction advantageously enables laterally different diagnostic findings to be highlighted, since laterally identical diagnostic findings typically cancel one another out due to the symmetry subtraction in the medical image dataset.

For the symmetry subtraction, it may be necessary in the first instance to determine a plane of symmetry of the organ system. This plane of symmetry is determined in particular in such a way that the mirroring of the first side onto the second side of the organ system is accomplished with a maximum degree of congruence. The first side and the second side of the organ system can then be localized on opposite sides of the plane of symmetry. In the typical case the aforementioned median plane of the examination subject will form the plane of symmetry. The symmetry subtraction can then be a mirroring of the first side of the organ system onto the second side of the organ system at the plane of symmetry, or vice versa. Furthermore, the symmetry subtraction can involve a registration, such as a non-rigid registration, of the first side and the second side of the organ system, as described in more detail below. Further processing steps deemed beneficial by those skilled in the art may also be performed during the symmetry subtraction.

The combination of the global image data subtraction and the symmetry subtraction proposed according to the invention affords a particularly advantageous further processing of the first medical image dataset and the second medical image dataset. The result image dataset that is thus obtained can contain particularly significant diagnostic information for those skilled in the particular field. For example, non-specific variations between the first medical image dataset and the second medical image dataset can be distinguished particularly easily from specific variations in the result image dataset.

A basic reason for this is that, according to the inventive approach, a physiological change and/or a change in an image background between the first medical image dataset and the second medical image dataset can be suppressed in the result image dataset on account of the symmetry subtraction. Performing the symmetry subtraction in addition to the global image data subtraction can thus ensure that pathological, in particular one-sided (unilateral), changes between the first medical image dataset and the second medical image dataset stand out particularly clearly in the result image dataset. For example, in the case of a take-up of contrast agent between the recording of the first and the second medical image dataset, an unwanted representation of the contrast agent uptake in healthy tissue can be suppressed in the result image dataset owing to the symmetry subtraction.

The inventive method furthermore offers the advantage that it is suitable for automatic execution, without interaction by a user. Thus, the inventive method can be carried out without prior knowledge about the localization of lesions. A manual segmentation of lesions for the purpose of the comparison between the first medical image dataset and the second medical image dataset can advantageously be dispensed with.

In an embodiment, the global image data subtraction is performed in a first step in which a global image data subtraction image dataset is generated, while the symmetry subtraction is performed in a second step within the global image data subtraction image dataset. In this way a subtraction of the first medical image dataset and the second medical image dataset with respect to time can be performed first, and then the symmetry subtraction can be performed in a single subtraction image dataset. This sequence of the global image data subtraction and the symmetry subtraction offers the advantage that only one symmetry subtraction needs to be performed. It is, however, also possible, as described below, to perform parts of the symmetry subtraction, for example a registration of image components and/or a specification of a plane of symmetry, before the global image data subtraction. The approach whereby preparations for the symmetry subtraction are made prior to the global image data subtraction and the actual symmetry subtraction is performed after the global image data subtraction offers the advantage that image information in the first medical image dataset and second medical image dataset that will be potentially be lost in the global image data subtraction can be used for the preparations for the symmetry subtraction.

In another embodiment, the symmetry subtraction involves a first symmetry subtraction and a second symmetry subtraction, wherein the first symmetry subtraction is performed within the first medical image dataset and the second symmetry subtraction is performed within the second medical image dataset in a first step, wherein a first symmetry subtraction image dataset and a second symmetry subtraction image dataset are generated, wherein the global image data subtraction is performed in a second step between the first symmetry subtraction image dataset and the second symmetry subtraction image dataset. In this approach the symmetry subtraction precedes the subtraction with respect to time. In this way image information in the first medical image dataset and in the second medical image dataset which will possibly be lost in the global image data subtraction can be used to optimum effect in the symmetry subtraction, for example for a registration of the two sides of the organ system.

In another embodiment, prior to the symmetry subtraction, a registration of the image components of the first side and the second side of the organ system is carried out, the image components of the first side and second side of the organ system registered to one another being subtracted from one another in the symmetry subtraction within the medical image dataset. Preferably, a non-rigid (elastic) registration of the image components is performed in this case. It is also possible to use a rigid registration or another registration technique known to those skilled in the art. The registration of the two sides of the organ system ensures that image components of the first side and the second side of the organ system, which image the same anatomical structures of the organ system, are subtracted from one another in the symmetry subtraction. Particularly advantageously, the first side and the second side of the organ system can be made congruent and/or mirror-symmetrical by the registration. Prior to the registration it can be beneficial in this case to mirror either the first side or the second side of the organ system, a mirrored side of the organ system being generated in the process. The registration can then be performed between the mirrored side and the side of the organ system disposed opposite the mirrored side.

In another embodiment, the registration takes place on the basis of the first medical image dataset and/or the second medical image dataset, with registration information being generated from the registration, and the image components of the first side and the second side of the organ system are registered with one another within the global image data subtraction image dataset using the registration information. The registration information can include a deformation matrix that results from the registration of the two sides of the organ system within the first medical image dataset and/or the second medical image dataset. The deformation matrix generated previously on the basis of the first medical image dataset and/or second medical image dataset can then be used for the symmetry subtraction within the global image data subtraction image dataset. In this case the deformation matrix can be applied to one side of the organ system in the global image data subtraction image dataset prior to the symmetry subtraction. Similarly, a specification of a plane of symmetry for the symmetry subtraction and/or a mirroring of image components of the global image data subtraction image dataset can also be carried out on the basis of image information of the first medical image dataset and/or second medical image dataset. Image information of the first medical image dataset and/or second medical image dataset can be used in this case before the global image data subtraction takes place. This approach is based on the consideration that image information of the first medical image dataset and/or second medical image dataset will potentially be lost in the global image data subtraction. This is because there may be too few structures recognizable in the global image data subtraction image dataset to enable a registration of the two sides of the organ system, or a registration that is sufficiently precise, using only image information of the global image data subtraction image dataset.

In another embodiment, the provision of the result image dataset is displaying the first side and/or the second side of the organ system, with subtraction values resulting from the global image data subtraction and the symmetry subtraction being represented by color coding, and with only one side of the organ system being displayed with color-coded subtraction values. It is also possible to display both sides of the organ system. In that case, positive subtraction values can be displayed in a first displayed side of the organ system, and negative subtraction values in a second displayed side of the organ system. Information relating to a laterality of a lesion can be inferred from the mathematical sign of a displayed subtraction value. The display of the first side and/or the second side of the organ system can be performed on the basis of information, in particular a user input, that indicates which side of the organ system potentially has a lesion and/or which signs of the subtraction values are conceivable for a lesion. If it is known, for example, that a lesion can lead to a diminution of signal intensities (in a perfusion study, for example), then the lesion can be visualized on the corresponding side of the two displayed sides of the organ system. The proposed possibilities for displaying the first side and/or the second side of the organ system can provide an observer skilled in the particular field, for example, with significant information about a change in image components between the recording of the first medical image dataset and the second medical image dataset.

In another embodiment, the acquisition of the first medical image dataset involves recording the first medical image dataset at a first point in time by operation of a medical imaging scanner, and the acquisition of the second medical image dataset involves recording the second medical image dataset at a second point in time by operation of a medical imaging scanner, and between the first point in time and the second point in time, a relevant event occurs that leads to a change in signal values between the first medical image dataset and the second medical image dataset. Such a relevant event may be, for example, a stimulus such as an optical or acoustic stimulus, to the examination subject, an administration of contrast agent, or some other intervention.

The evaluation computer according to the invention has an input or port to receive a first medical image dataset and a second medical image dataset, and a processor that has a first subtraction unit and a second subtraction unit configured to perform processing of the first and second datasets as described above. An output unit provides the processing result as a data file for viewing.

In this way the evaluation computer is embodied for performing a method for evaluating medical image data that represent an organ system of an examination subject, the organ system having a first side and a second side which are characteristically bilaterally symmetrical to one another. The first medical image dataset of the organ system of the examination subject and the second medical image dataset of the organ system of the examination subject are provided to the processor, that processes the first medical image dataset and the second medical image dataset to obtain a result image dataset. The first subtraction unit is configured to perform a global image data subtraction in which image components of the first medical image data and the second medical image data are subtracted from one another. The second subtraction unit is configured to perform a symmetry subtraction in which image components of the first side and the second side of the organ system are subtracted from one another within a medical image dataset. The output unit is configured to provide the result image dataset as an output.

According to an embodiment of the evaluation computer, the first subtraction unit and the second subtraction unit are configured to implement the global image data subtraction in a first step, a global image data subtraction image dataset being thereby generated, and to implement the symmetry subtraction in a second step within the global image data subtraction image dataset.

According to another embodiment of the evaluation computer, the first subtraction unit and the second subtraction unit are configured to perform the symmetry subtraction as a first symmetry subtraction and a second symmetry subtraction, the first symmetry subtraction being carried out within the first medical image dataset and the second symmetry subtraction being carried out within the second medical image dataset in a first step, a first symmetry subtraction image dataset and a second symmetry subtraction image dataset thereby being generated. The global image data subtraction takes place in a second step between the first symmetry subtraction image dataset and the second symmetry subtraction image dataset.

According to another embodiment of the evaluation computer, the second subtraction process is configured to perform, prior to the symmetry subtraction, a registration of the image components of the first side and the second side of the organ system, wherein the image components of the first side and the second side of the organ system that are registered to one another are subtracted from one another in the symmetry subtraction within the medical image dataset.

According to another embodiment of the evaluation computer, the first subtraction processor and the second subtraction processor are configured to implement the registration on the basis of the first medical image dataset and/or the second medical image dataset, with registration information being generated from the registration, and the image components of the first side and the second side of the organ system within the global image data subtraction image dataset being registered with one another using the registration information.

According to another embodiment of the evaluation computer, the output unit is configured to provide the result image dataset by displaying the first side and/or the second side of the organ system, with subtraction values resulting from the global image data subtraction and the symmetry subtraction being represented by color coding.

According to another embodiment of the evaluation computer, the first medical image dataset is a recording at a first point in time by operation of a medical imaging scanner and the second medical image dataset is a recording at a second point in time by operation of the medical imaging device, and between the first point in time and the second point in time, a relevant event occurs, which leads to a change in signal values between the first medical image dataset and the second medical image dataset.

The medical imaging apparatus according to the invention has an evaluation computer according to the invention. The evaluation computer is configured to send control signals to the medical imaging scanner and/or to receive and/or process control signals in order to carry out the method according to the invention. The evaluation computer can be integrated into the medical imaging apparatus. The evaluation computer can also be installed separately from the medical imaging scanner. The evaluation computer can be connected to the medical imaging scanner. The acquisition of the first medical image dataset is a recording of the first medical image dataset by operation of a scanner of the medical imaging apparatus. The acquisition of the second medical image dataset also is a recording of the second medical image dataset by operation of the scanner of the medical imaging apparatus. The first medical image dataset and the second medical image dataset are then transferred to the evaluation computer for further processing. The evaluation computer thus acquires the first medical image dataset and the second medical image dataset by controlling operation of the scanner.

The invention also encompasses a non-transitory, computer-readable data storage medium that can be loaded directly into a memory of a programmable evaluation computer and program code that cause the computer to implement the method according to the invention when the program code is executed in the evaluation computer. As a result the method according to the invention can be executed quickly and in an identically reproducible and robust manner. The computer must fulfill certain requirements, such as having a suitable random access memory, a suitable graphics card or a suitable logic unit, so that the method steps can be performed efficiently. Examples of electronically readable data media are a DVD, a magnetic tape or a USB stick on which electronically readable control information, in particular software, is stored.

The advantages of the evaluation computer according to the invention, the medical imaging apparatus according to the invention and the storage medium according to the invention substantially correspond to the advantages of the method according to the invention, which have been explained in detail above. Features, advantages and alternative embodiment variants cited in connection with the method are applicable to the other aspects of the invention. The functional features of the method are embodied by corresponding device-related modules, in particular by hardware modules.

BRIEF DESCRIPTION OF THE DRAWINGS

FIG. 1 schematically illustrates a medical imaging apparatus according to the invention having an evaluation computer according to the invention.

FIG. 2 is a flowchart of a first embodiment of the method according to the invention.

FIG. 3 is a flowchart of a second embodiment of the method according to the invention.

FIG. 4 is a flowchart of a third embodiment of the method according to the invention.

DESCRIPTION OF THE PREFERRED EMBODIMENTS

FIG. 1 shows a medical imaging apparatus according to the invention comprising an evaluation computer 33 according to the invention in a block diagram.

The medical imaging apparatus can be, for example, a magnetic resonance apparatus, a single-photon emission tomography (SPECT) apparatus, a positron emission tomography (PET) apparatus, a computed tomography (CT), an ultrasound device, an X-ray device or a C-arm device. Combined medical imaging apparatuses formed by any desired combination of a number of the cited imaging modalities are also possible. In the case shown the medical imaging apparatus is embodied as an example as a magnetic resonance apparatus 11.

The magnetic resonance apparatus 11 has a detector unit formed by a scanner 13 that has a basic field magnet 17 for generating a strong and constant basic magnetic field 18. The magnetic resonance scanner 13 has a cylinder-shaped patient receiving zone 14 for accommodating an examination subject 15, in the present case a patient, the patient receiving zone 14 is cylindrically enclosed by the scanner 13 in a circumferential direction. The patient 15 can be introduced into the patient receiving zone 14 by a patient support 16 of the scanner 13. For this purpose the patient support 16 has a patient support table that is movable inside the scanner. The scanner 13 is shielded externally by a housing shell 31.

The scanner 13 additionally has a gradient coil arrangement 19 for generating magnetic field gradients that are used for spatial encoding during imaging. The gradient coil arrangement 19 is actuated by a gradient control processor 28. The scanner 13 furthermore has a radiofrequency antenna unit 20, which in the case shown is a body coil permanently integrated into the scanner 13, and a radiofrequency antenna control processor 29. The radiofrequency antenna unit 20 is actuated by the radiofrequency antenna control unit 29 and radiates radiofrequency magnetic resonance sequences into an examination chamber that is substantially formed by the patient receiving zone 14, to cause nuclear spins in the patient 15 to deviate from the polarization that is established in the main magnetic field 18 generated by the main magnet 17. The radiofrequency antenna unit 20 is furthermore designed to receive magnetic resonance signals from the patient 15 that result when the nuclear spins relax from the excitation produced by the radiofrequency sequence.

The magnetic resonance apparatus 11 has a computer 24 for controlling the basic field magnet 17, the gradient control processor 28 and the radiofrequency antenna control processor 29. The computer unit 24 is responsible for the centralized control of the magnetic resonance apparatus 11, such as performing a predetermined imaging gradient echo sequence. Control information such as imaging parameters, as well as reconstructed magnetic resonance images, can be provided for a user on a presentation unit, in the present case a display monitor 25, of the magnetic resonance apparatus 11. The magnetic resonance apparatus 11 additionally has an input interface 26 via which information and/or parameters can be entered by a user during a measurement procedure. The computer 24 can include the gradient control processor 28 and/or the radiofrequency antenna control processor 29 and/or the display monitor 25 and/or the input interface 26.

The illustrated magnetic resonance apparatus 11 can of course have further components that are ordinarily present in magnetic resonance apparatuses. The basic operation of a magnetic resonance apparatus is known to those skilled in the art, so a detailed description of the further components is not necessary herein.

The depicted evaluation computer 33 has a first image data acquisition input 34, a second image data acquisition input 35, an output unit 36, and a processor 37 that includes a first subtraction processor 38 and a second subtraction processor 39. The first and second image data acquisition inputs may be formed by the same (i.e., a common) input port.

The scanner 13, serving as an image data acquisition, unit is designed for recording a first medical image dataset and a second medical image dataset. The first image data acquisition input 34 and the second image data acquisition input 35 of the evaluation unit 33 then receive the first medical image dataset and the second medical image dataset from the computer 24 of the magnetic resonance apparatus 11. For this purpose the first image data acquisition input 34 and the second image data acquisition input 35 are connected to the computer unit 24 of the magnetic resonance apparatus 11 in order to enable an exchange of data. In this configuration the output unit 36 is connected to the display monitor 25 of the magnetic resonance apparatus 11 so that a result image dataset determined by the evaluation computer 33 can be displayed. The magnetic resonance apparatus 11 is therefore configured together with the evaluation computer 33 for the purpose of performing the method according to the invention for evaluating medical image data.

Alternatively to the display, the evaluation computer 33 can be configured in isolation for the purpose of performing the method according to the invention for evaluating medical image data. To that end, the first image data acquisition input 34 and the second image data acquisition input 35 of the evaluation computer 33 will load image data from a database and/or retrieve image data from a connected medical imaging apparatus.

FIG. 2 shows a flowchart of a first embodiment of the method according to the invention for evaluating medical image data. The medical image data in this case image an organ system of an examination subject 15, the organ system having a first side and a second side which are characteristically bilaterally symmetrical to one another.

In a first method step 40, a first medical image dataset of the organ system of the examination subject 15 is received by the first image data acquisition input 34.

In a further method step 41, a second medical image dataset of the organ system of the examination subject is received by the second image data acquisition input 35.

In a further method step 42, the first medical image dataset and the second medical image dataset are processed by the processor 37, so as to generate a result image dataset. The further method step 42 in this case has a sub-step 42T in which a global image data subtraction is performed by the first subtraction processor 38, in which image components of the first medical image data and the second medical image data are subtracted from one another. The further method step 42 includes a sub-step 42S in which a symmetry subtraction is performed by the second subtraction processor 39, in which image components of the first side and the second side of the organ system are subtracted from one another within a medical image dataset.

In a further method step 43, the result image dataset is provided in electronic form by the output unit 36.

FIG. 3 shows a flowchart of a second embodiment of a method according to the invention for evaluating medical image data.

The following description is limited essentially to the differences compared to the exemplary embodiment in FIG. 2, reference being made to the description of the exemplary embodiment in FIG. 2 with regard to method steps that remain the same. Method steps that remain substantially the same are labeled with the same reference numerals.

The embodiment variant of the method according to the invention shown in FIG. 3 includes the method steps 40, 41, 42, 42T, 42S, 43 of the first embodiment of the inventive method according to FIG. 2. The embodiment variant of the method according to the invention shown in FIG. 3 has additional method steps and sub-steps. An alternative method execution sequence to FIG. 3, which includes only some of the additional method steps and/or sub-steps represented in FIG. 2, is also conceivable. An alternative method execution sequence to FIG. 3 can also include additional method steps and/or sub-steps.

In a further method step 44, a relevant event takes place intermediately in time between the recording of the first medical image dataset at a first point in time in the further method step 40 and the recording of the second medical image dataset at a second point in time in the further method step 41. This relevant event, such as an administration of contrast agent, leads to a change in signal values between the first medical image dataset and the second medical image dataset. The first medical image dataset accordingly mirrors a state of the examination subject 15 prior to the relevant event and the second medical image dataset mirrors a state of the examination subject 15 after the relevant event.

In the case shown, the global image data subtraction is performed in the further method step 42 in sub-step 42T prior to the symmetry subtraction in sub-step 42S. During the processing of the first medical image dataset and the second medical image dataset in the further method step 42, the global image data subtraction is performed in a sub-step 42T of the further method step 42, a global image data subtraction image dataset being generated in the process. The symmetry subtraction then takes place in a further sub-step 42S within the global image data subtraction image dataset.

Prior to the symmetry subtraction, a registration of the image components of the first side and the second side of the organ system takes place in a further sub-step 42R. In the symmetry subtraction, the image components of the first side and second side of the organ system registered to one another can then be subtracted from one another within the subtraction image dataset.

In the case shown, the registration is accomplished in a further sub-step 42P on the basis of the first medical image dataset and/or the second medical image dataset. With the use of the registration, registration information is generated, the image components of the first side and the second side of the organ system within the global image data subtraction image dataset being registered onto one another using the registration information in the further sub-step 42R.

Furthermore, a symmetry axis can be specified and/or one side of the organ system can be mirrored onto the opposite side in the further sub-step 42P on the basis of the first medical image dataset and/or the second medical image dataset. The specified symmetry axis and/or information from the mirroring can then be registered during the registration on the basis of the first medical image dataset and/or the second medical image dataset in the further sub-step 42P.

In the further method step 43, providing the result image dataset as an electronic output, the first side and/or the second side of the organ system are/is then displayed in a sub-step 43D, subtraction values resulting from the global image data subtraction in sub-step 42T and the symmetry subtraction in sub-step 42R being represented by color coding. The result is accordingly visualized in particular in a false color rendering.

FIG. 4 shows a flowchart of a third embodiment of the method according to the invention for evaluating medical image data.

The following description is limited essentially to the differences compared to the exemplary embodiment in FIG. 2, reference being made to the description of the exemplary embodiment in FIG. 2 with regard to method steps that remain the same. Method steps that remain substantially the same are labeled with the same reference numerals.

The embodiment of the method according to the invention shown in FIG. 4 includes the method steps 40, 41, 42, 42T, 42S, 43 of the first embodiment of the method according to the invention as shown in FIG. 2. The embodiment variant of the method according to the invention shown in FIG. 4 includes additional method steps and sub-steps. An alternative method execution sequence to FIG. 4, which includes only some of the additional method steps and/or sub-steps represented in FIG. 2, is also conceivable. An alternative method execution sequence to FIG. 4 can also include additional method steps and/or sub-steps.

In the case shown, the symmetry subtraction is performed in the further method step 42 in sub-step 42S prior to the global image data subtraction in sub-step 42T. Thus, the symmetry subtraction comprises a first symmetry subtraction in a sub-step 42S1 and a second symmetry subtraction in a sub-step 42S2, the first symmetry subtraction being performed within the first medical image dataset and the second symmetry subtraction being performed within the second medical image dataset.

During this process, a first symmetry subtraction image dataset and a second symmetry subtraction image dataset are generated. The global image data subtraction is then performed between the first symmetry subtraction image dataset and the second symmetry subtraction image dataset.

Additional steps from the embodiment according to FIG. 3, for example a registration of the sides of the organ system, can be performed in this case as well.

The symmetry subtraction comprises a first symmetry subtraction and a second symmetry subtraction, the first symmetry subtraction being performed within the first medical image dataset and the second symmetry subtraction being performed within the second medical image dataset in a first step, a first symmetry subtraction image dataset and a second symmetry subtraction image dataset being generated in the process, the global image data subtraction being performed in a second step between the first symmetry subtraction image dataset and the second symmetry subtraction image dataset.

The method steps of the method according to the invention shown in FIGS. 2-4 are performed by the evaluation computer 33. For this purpose, the evaluation computer 33 has the necessary software and/or computer programs, which are stored in a memory unit of the evaluation computer 33. The software and/or computer programs comprise program means which are configured to perform the method according to the invention when the computer program and/or the software are/is executed in the evaluation computer 33 by means of a processor unit of the evaluation computer 33.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for evaluating medical image data comprising:
providing a first medical image dataset of an organ system of an examination subject to a computer, said organ system having a first side and a second side that are characteristically bilaterally symmetrical with respect to each other, said first medical image dataset comprising first medical image data comprising first image components;
providing said computer with a second medical image dataset of said organ system, said second medical image dataset comprising second medical image data comprising second image components;
in said computer, processing said first medical image dataset and said second medical image dataset in a processing algorithm to obtain a result image by, in said processing algorithm, executing a global image data subtraction wherein said first image components of said first medical image data and said second image components of said second medical image data are subtracted from one another in order to obtain a global image data subtraction image dataset, and thereafter executing a symmetry subtraction, within said global image subtraction data set, in which symmetry subtraction image components of the first side and the second side of the organ system are subtracted from one another; and
making said result image dataset available in electronic form from said computer as a data file.

2. A method as claimed in claim 1 comprising, before said symmetry subtraction, bringing image components of the first side and image components of the second side of the organ system, within said global image data subtraction dataset, into registration with each other.

3. A method as claimed in claim 1 wherein said symmetry subtraction comprises a first symmetry subtraction and a second symmetry subtraction, and executing said first symmetry subtraction within said first medical image dataset to obtain a first symmetry subtraction image dataset and executing said second symmetry subtraction within said second medical image dataset to obtain a second symmetry subtraction image dataset, and executing said global image data subtraction between said first symmetry subtraction image dataset and said second symmetry subtraction image dataset.

4. A method as claimed in claim 3 comprising, prior to said symmetry subtraction, bringing said image components of the first side and the image components of the second side of the organ system into registration with each other within each of said first medical image dataset and said second medical image dataset.

5. A method as claimed in claim 1 comprising providing said data file of said result image dataset to a display monitor in communication with said computer and, at said display monitor, displaying at least one of said first side and said second side of said organ system with subtraction values resulting from said global image data subtraction and said symmetry subtraction being represented by color coding.

6. A method as claimed in claim 1 comprising providing said computer with said second medical image dataset that was acquired with a medical imaging apparatus at a point in time after acquisition of said first medical image dataset with said medical imaging apparatus, and wherein an event has occurred in said examination subject between the respective times of acquisition of said first and second medical image datasets, and comprising executing said processing algorithm in said computer to obtain said result image dataset with a representation of said event in said result image dataset.

7. An evaluation computer comprising:
an input configured to receive a first medical image dataset of an organ system of an examination subject to a computer, said organ system having a first side and a second side that are characteristically bilaterally symmetrical with respect to each other, said first medical image dataset comprising first medical image data comprising first image components, and to receive a second medical image dataset of said organ system, said second medical image dataset comprising second medical image data comprising second image components;
said computer being configured to process said first medical image dataset and said second medical image dataset in a processing algorithm to obtain a result image by, in said processing algorithm, executing a global image data subtraction wherein said first image components of said first medical image data and said second image components of said second medical image data are subtracted from one another in order to obtain a global image data subtraction image dataset, and thereafter executing a symmetry subtraction, within said global image subtraction data set, in which symmetry subtraction image components of the first side and the second side of the organ system are subtracted from one another; and
said computer being configured to make said result image dataset available in electronic form from said computer as a data file.

8. A medical imaging apparatus comprising:
a medical imaging scanner;
a control computer configured to operate the medical imaging scanner to obtain a first medical image dataset and a second medical image dataset of an organ system of an examination subject to a computer, said organ system having a first side and a second side that are characteristically bilaterally symmetrical with respect to each other, said first medical image dataset comprising first medical image data comprising first image components, and said second medical image dataset comprising second medical image data comprising second image components;

said computer being configured to process said first medical image dataset and said second medical image dataset in a processing algorithm to obtain a result image by, in said processing algorithm, executing a global image data subtraction wherein said first image components of said first medical image data and said second image components of said second medical image data are subtracted from one another in order to obtain a global image data subtraction image dataset, and thereafter executing a symmetry subtraction, within said global image subtraction data set, in which symmetry subtraction image components of the first side and the second side of the organ system are subtracted from one another, said first medical image dataset, and said second medical image dataset, to obtain said result image dataset; and make said result image dataset available in electronic form from said computer as a data file.

9. A non-transitory, computer-readable data storage medium encoded with programming instructions, said storage medium being loaded into an evaluation computer of a medical imaging apparatus, and said programming instructions causing said evaluation computer to:

receive a first medical image dataset of an organ system of an examination subject to a computer, said organ system having a first side and a second side that are characteristically bilaterally symmetrical with respect to each other, said first medical image dataset comprising first medical image data comprising first image components;

receive a second medical image dataset of said organ system, said second medical image dataset comprising second medical image data comprising second image components;

process said first medical image dataset and said second medical image dataset in a processing algorithm to obtain a result image by, in said processing algorithm, executing a global image data subtraction wherein said first image components of said first medical image data and said second image components of said second medical image data are subtracted from one another in order to obtain a global image data subtraction image dataset, and thereafter executing a symmetry subtraction, within said global image subtraction data set, in which symmetry subtraction image components of the first side and the second side of the organ system are subtracted from one another within a same image dataset, before or after said global image data subtraction; and make said result image dataset available in electronic form from said computer as a data file.

* * * * *